(12) United States Patent (10) Patent No.: US 7,696,180 B2
Sugiyama (45) Date of Patent: Apr. 13, 2010

(54) THERAPEUTIC AGENTS FOR TREATMENT OF SOLID TUMORS COMPRISING AN EXPRESSION-INHIBITING SUBSTANCE AGAINST WILMS' TUMOR GENE (WT1)

(76) Inventor: Haruo Sugiyama, 2-19-30, Senbanishi, Mino-shi, Osaka (JP)

( * ) Notice: Subject to any disclaimer, the term of this patent is extended or adjusted under 35 U.S.C. 154(b) by 0 days.

(21) Appl. No.: 11/320,481

(22) Filed: Dec. 29, 2005

(65) Prior Publication Data

US 2006/0105981 A1 May 18, 2006

Related U.S. Application Data

(60) Division of application No. 10/171,639, filed on Jun. 17, 2002, now abandoned, which is a continuation of application No. 09/462,307, filed as application No. PCT/JP98/03198 on Jul. 16, 1998, now abandoned.

(30) Foreign Application Priority Data

Jul. 16, 1997 (JP) .................................... 9-191635

(51) Int. Cl.
C07H 21/02 (2006.01)
C07H 21/04 (2006.01)
A61K 31/70 (2006.01)
A01N 43/04 (2006.01)

(52) U.S. Cl. ........................ 514/44; 536/23.1; 536/24.3; 536/24.33; 536/24.5

(58) Field of Classification Search .................. 514/44; 536/23.1, 24.3, 24.33, 24.5
See application file for complete search history.

(56) References Cited

U.S. PATENT DOCUMENTS 6,034,235 A 3/2000 Sugiyama et al.

FOREIGN PATENT DOCUMENTS

| JP | 9-104629 | 4/1997 |
|---|---|---|
| WO | WO 95/29995 | 11/1995 |
| WO | WO 96/38176 | 12/1996 |
| WO | WO 96/38276 | 12/1996 |
| WO | WO 97/39354 | 10/1997 |

OTHER PUBLICATIONS

Braasch et al. Novel Anttisense and Peptide Nucleic Acid Strategies for Controlling Gene Expression. (Biochemistry, vol. 41, pp. 4503-4510).*
Tamm et al. Antisense therapy in oncology: new hope for an old idea? (The Lancet, 2001 vol. 358 pp. 489-497).*
Sharma et al. The therapeutic potential of antisense oligonucleotides. BioEssays, 1995, vol. 17, 1055-1063.*
Juliano et al. Antisense pharmacodynamics: Critical issues in the transport and delivery of antisense oligonucleotides. Pharmaceutical Research, 1999 vol. 16:494-502.*

(Continued)

*Primary Examiner*—Sean McGarry
*Assistant Examiner*—Terra Cotta Gibbs
(74) *Attorney, Agent, or Firm*—Foley & Lardner LLP (57) ABSTRACT

The present invention relates to therapeutic agents for treatment of solid tumors comprising an expression-inhibiting substance (an antisense oligonucleotide derivative, a WT1 mutant gene, a WT1 mutant protein, a low molecular weight substance, and the like) against the Wilms' tumor gene (WT1).

6 Claims, 7 Drawing Sheets

OTHER PUBLICATIONS

Kudoh et al. Constitutive expression of the Wilms tumor suppressor gene WT1 in F9 embryonal carcinoma cells induces apoptotic cell deatch in response to retinoic acid. Oncogene, 1996 vol. 13, pp. 1431-1439.*

Nielsen, PE (Gene Therapy, 2005 vol. 12:956-957).*

Agrawal et al., "Antisense therapeutics: is it as simple as complementary base recognition?" *Molecular Medicine Today*, 2000, vol. 6: 72-81.

Agrawal S., "Antisense oligonucleotides: towards clinical trial," TIBTECH (Oct. 1996) 14:376-387.

Amin, Kunjiata M. et al., "Wilms' Tumor 1 Susceptibility (WT1) Gene Products are Selectively Expressed in Malignant Mesothelioma", *American Journal of Pathology*, vol. 146, No. 2, Feb. 1995, pp. 344-356.

Berendsen, "A glimpse of the holy grail," Science (Oct. 1998) 282:642-643.

Branch, A.D., "A good antisense molecule is hard to find," TIBS 23, (Feb. 1998), pp. 45-50.

Bruening, W. et al., "Analysis of the 11p13 Wilms' Tumor Suppressor Gene (WT1) in Ovarian Tumors," Cancer Investigation (1993), 11(4):393-399.

Gerald, W.L. et al., "Rapid Communication: Expression of the 11p13 Wilms' Tumor Gene, WT1, Correlates with Histologic Category of Wilms' Tumor," American Journal of Pathology (May 1992), 140(5):1031-1037.

Gerwitz et al., "Facilitating oligonucleotide deliver: Helping antisense deliver on its promise," Proc. Natl. Acad. Sci., USA, (Apr. 1996) 93:3161-3163.

Green et al., "Antisense oligonucleotides: An evolving technology for the modulation of gene expression in human disease", *J. Am Coll Surg*, 2000, vol. 191: 93-105.

Haber, D.A. et al., "Alternative splicing and genomic structure of the Wilms Tumor gene WT1," Proc. Natl. Acad. Sci. USA (Nov. 1991) 88:9618-9622.

Jen et al., "Suppression of gene expression by targeted disruption of messenger RNA: Available options and current strategies", *Stem Cells*, 2000, vol. 18: 307-319.

Lacoste et al., "Triple helix formation with purine rich phophorothioate containing oligonucleotides covalently linked to an acridine derivative," NAR (1997) 25(10):1991-1998.

Rauscher, F.J., III, et al. "Characterization of Monoclonal Antibodies Directed to the Amino-Terminus of the WT1, Wilms' Tumor suppressor Protein," Hybridoma (1988) 17(2):191-198.

Rothenpieler et al., "Antisense oligodeoxynucleotides directed against Wilms tumor gene wt1 inhibit kidney differentiation and development," J. Am. Soc. Nephr. (Sep. 1993), 5(3):635 6p.

Silberstein, G.B. et al., "Altered expression of the WT1 tumor suprssor Gene in human breast cancer," Proc. Natl. Acad. Sci. USA (Jul. 1997) 94:8132-8137.

Waters, Justin S. et al., "Phase I Clinical and Pharmacokinetic Study of Bcl-2 Antisense Oligonucleotide Therapy in Patients with Non-Hodgkin's Lymphoma", Journal of Clinical Oncology, vol. 18, No. 9, 2000, pp. 1812-1823.

Yamagami et al., "Growth inhibition of human leukemic cells by wt1 (Wilms tumor gene) antisense oligodeoxynucleotides: implications for the involvement of wt1 in leukemogenesis," Blood (Apr. 1996) 87(7):2878-2884.

Yamagami, T. et al., "Growth Inhibition of Human Leukemic Cells by WT1 (Wilms Tumor Gene) Antisense Oligodeoxynucleotides: Implications for the Involvement of WT1 in Leukemogenesis," Blood (Apr. 1996) 87(7):2878-2884.

Algar et al., "A WT1 antisense oligonucleotide inhibits proliferation and induces apoptosis in myeloid leukaemia cell lines," Oncogene, 1996, 12:1005-1014.

Coppes et al., "Analysis of WT1 in Granulosa Cell and Other Sex-Cord Stromal Tumors," Cancer Research, Jun. 15, 1993, 53:2712-2714.

* cited by examiner

THERAPEUTIC AGENTS FOR TREATMENT OF SOLID TUMORS COMPRISING AN EXPRESSION-INHIBITING SUBSTANCE AGAINST WILMS' TUMOR GENE (WT1)

This application is a divisional application of U.S. patent application Ser. No. 10/171,639, filed Jun. 17, 2002, now abandoned which is a continuation application of U.S. patent application Ser. No. 09/462,307, now abandoned, filed Jan. 6, 2000, which is the National Stage of International Application No. PCT/JP98/03198, filed Jul. 16, 1998, which claims the priority to Japan Application No. 09-191635, filed Jul. 16, 1997, which are all incorporated herein by reference.

TECHNICAL FIELD

The present invention relates to therapeutic agents for treatment of solid tumors comprising an expression-inhibiting substance against Wilms' tumor gene (WTI).

BACKGROUND ART

Wilms' tumor is a pediatric kidney tumor resulting from the inactivation of both alleles of the Wilms' tumor gene (WT1) located on chromosome 11p13 (Call K M et al., Cell 60: 509, 1990). The non-coding upstream sequence of WT1 (C. E. Camphell et al., Oncogene 9: 583-595, 1994) and the coding region including introns (D. A. Haber et al., Proc. Natl. Acad. Sci. U.S.A., 88:9618-9622 (1991)) have already been reported, and they are expected to be responsible for the growth and differentiation of tumors and the like (D. A. Haber et al., supra).

Based on the association of WT1 with the growth of leukemia cells, the present inventors have found that an antisense oligonucleotide derivative against WT1 suppresses and/or inhibits the growth of leukemia cells (PCT Patent Publication WO96/38176, and T. Yamagami, et al., Blood, 87(7) 2878-2884 (1996)). It is not known, however, if an expression-inhibiting agent of WT1 suppresses and/or inhibits the growth of solid tumors.

DISCLOSURE OF THE INVENTION

Thus, the present invention provides a therapeutic agent for treatment of solid tumors comprising an expression-inhibiting substance against Wilms' tumor gene (WTI).

BEST MODE FOR CARRYING OUT THE INVENTION

The present invention provides a therapeutic agent, for treatment of solid tumors, comprising an expression-inhibiting substance against WTI. Solid tumors, as used herein, mean, for example, gastric cancer, colon cancer, lung cancer, breast cancer, embryonic cell cancer, hepatic cancer, skin cancer, cystic cancer, prostate cancer, uterine cancer, cervical cancer, ovary cancer, and the like. The expression-inhibiting substance for use in the present invention may be any substance that inhibits the expression of WT1 and includes, for example, an antisense oligonucleotide derivative against WT1, a low molecular weight inhibiting substance such as a WT1 mutant gene, a mutant protein and decoy DNA etc. that act on WT1 in a dominant negative manner, or a low molecular weight inhibiting substance such as a peptide that inhibits transcription activity by specifically binding to WT1, and the like. The antisense oligonucleotide derivative for use in the present invention may be an antisense oligonucleotide derivative against WT1 including, for example, one against the transcription capping site of WT1, one against the translation initiation region, an exon or an intron, and the like.

For example, a nucleotide sequence of a sense DNA strand in a region containing the transcription capping site of WT1 is represented by SEQ ID NO: 9 and nucleotide sequences of the sense DNA strands of exon 1 to 10 in the coding region of WT1 are represented by SEQ ID NO: 10 to 19, respectively. The present invention employs antisense oligonucleotide derivatives against such nucleotide sequences of the sense DNA strands of WT1. The antisense oligonucleotide derivative is an antisense oligonucleotide derivative comprising 5 to 50, preferably 9 to 30 contiguous nucleotides of an antisense DNA strand or an RNA strand of WT1, or 5 to 70, preferably 9 to 50 intermittently or partially complementary nucleotides, provided that it can bind to the DNA strand or the RNA strand of WT1.

As the one against a transcription capping site, there may be mentioned the following nucleotide sequences: 5'-AGGGTCGAATGCGGTGGG-3' (SEQ ID NO: 2) and 5'-TCAAATAAGAGGGGCCGG-3' (SEQ ID NO: 4). Furthermore, as the one against a translation initiation region, there may be mentioned antisense oligonucleotide derivatives against the translation initiation codon ATG and a region containing the upstream and/or the downstream thereof including, for example, the following nucleotide sequence: 5'-GTCGGAGCCCATTTGCTG-3' (SEQ ID NO: 6).

The coding region of WT1 contains 10 exons. The antisense oligonucleotide derivative of the present invention is directed against a sequence contained in any of these exons, a sequence covering any of two contiguous exons after splicing, a sequence covering a contiguous intron and exon, and a sequence of any intron and 3' or 5'-end non-coding region. One example is against the sixth exon that has the following sequence: 5'-CGTTGTGTGGTTATCGCT-3' (SEQ ID NO: 8).

Furthermore, the region corresponding to the antisense oligonucleotide derivative of the present invention having a nucleotide sequence that is intermittently or partially complementary to the DNA strand or the RNA strand of WT1 includes, but not limited to, a ribozyme having a function of cleaving any region of a DNA strand or of an RNA strand of WT1.

The structure of the antisense oligonucleotide derivative for use in the present invention is as shown in Chemical formula (1) wherein x may be independently any of oxygen (O), sulfur (S), a lower alkyl group and a primary amine or a secondary amine; Y may be independently any of oxygen (O) and sulfur (S); Z is hydrogen or a hydroxyl group; when Z is hydrogen B is selected from the group consisting of adenine, guanine, thymine and cytosine, and when Z is a hydroxyl group B is selected from the group consisting of adenine, guanine, uracil and cytosine, and B is primarily a complementary oligonucleotide to the DNA or the mRNA encoding WT1; R is independently hydrogen or a dimethoxytrityl group or a lower alkyl group; and n is 7 to 28.

(I)

Preferred antisense oligonucleotide derivatives include not only non-modified antisense oligonucleotides but also modified antisense oligonucleotides. Examples of such modifications include, for example, lower alkyl phosphonate-modifications such as the above-mentioned methylphosphonate type or the ethylphosphonate type, and the phosphorothioate modifications or the phosphoroamidate modifications (see Chemical formula (2)).

Examples of

-continued

Methylphosphoante

Phosphorothioate

Phosphorodithioate

Phosphoroamidate

Triester phosphate

These antisense oligonucleotide derivatives can be obtained by a conventional method as shown below.

An antisense oligonucleotide of Formula (1) in which X and Y are O and Z is hydrogen or a hydroxyl group may be readily synthesized using a commercially available DNA synthesizer (for example the one manufactured by Applied Biosystems).

Synthesis of an antisense oligodeoxy ribonucleotide in which Z is hydrogen can be effected by the solid phase synthesis using phosphoroamidite, the solid phase synthesis using hydrogen phosphonate, or the like.

See, for example, T. Atkinson, M. Smith, in Oligonucleotide Synthesis: A Practical Approach, ed. M. J. Gait, IRL Press, 35-81 (1984); M. H. Caruthers, Science, 230, 181 (1985); A. Kume, M. Fujii, M. Sekine, M. Hata, J. Org. Chem., 49, 2139 (1984); B. C. Froehler, M. Matteucci, Tetrahedron Lett., 27, 469 (1986); P. J. Garegg, I. Lindh, T. Regberg, J. Stawinski, R. Stromberg, C. Henrichson, ibid, 27, 4051 (1986); B. S. Sproat, M. J. Gait, in Oligonucleotide Synthesis: A Practical Approach, ed. M. J. Gait, IRL Press, 83-115 (1984); S. L. Beaucage and M. H. Caruthers, Tetrahedron Lett., 22, 1859-1862 (1981); M. D. Matteucci and M.

H. Caruthers, Tetrahedron Lett., 21, 719-722 (1980); M. D. Matteucci and M. H. Caruthers, J. Am. Chem. Soc., 103, 3185-3191 (1981)

A triester phosphate modification derivative in which X is a lower alkoxy group can be obtained by, for example, a conventional method in which an oligonucleotide that was obtained by chemical synthesis is treated with a solution of tosyl chloride in DMF/methanol/2,6-lutidiene (Moody H. M. et al., Nucleic Acids Res., 17, 4769-4782 (1989)).

An alkyl phosphonate modification derivative in which X is an alkyl group can be obtained by, for example, using phosphoamidite (M. A. Dorman, et al., Tetrahedron, 40, 95-102 (1984); K. L. Agarwal and F. Riftina, Nucleic Acids Res., 6, 3009-3024 (1979)).

A triester phosphorothioate modification derivative in which X is S can be obtained by a solid phase synthesis using sulfur (C. A. Stein, et al., Nucleic Acids Res., 16, 3209-3221 (1988)), or a solid phase synthesis using tetraethyltiraum disulfide (H. Vu and B. L. Hirschbein, Tetrahedron Letters, 32, 3005-3008 (1991).

A phosphorodithioate modification derivative in which both X and Y are S can be obtained by, for example, a solid phase synthesis in which a bisamidite is converted to a thioamidite, to which is added sulfur to yield said modification (W. K.-D. Brill, et al., J. Am Chem. Soc., 111, 2321-2322 (1989)).

A phosphoroamidate modification derivative in which X is a primary amine or a secondary amine can be obtained by, for example, a solid phase synthesis in which hydrogen phosphonate is treated with a primary or secondary amine (B. Froehler, et al., Nucleic Acids Res., 16, 4831-4839 (1988)). Alternatively the amidite may be oxidized with tert-butyl hydroperoxide to yield said modification (H. Ozaki, et al., Tetrahedron Lett., 30, 5899-5902 (1989)).

Although the synthetic method of an antisense oligoribonucleotide in which Z is a hydroxyl group is very complicated as compared to that of an antisense oligodeoxyribonucleotide in that a 2'-hydroxyl group present in the ribose (sugar) must be protected in the former method, it can be synthesized by selecting, as appropriate, the protecting group and the method of phosphorylation (see Biseibutugaku Kiso Koza (Basic Course in Microbiology), Vol. 8, Eiko Ohtsuka and Kazunobu Miura, Idenshi Kogaku (Genetic Engineering), Tadahiko Ando and Kenji Sakaguchi ed., Oct. 10, 1987, Kyoritsu Shuppan Publishing Company).

Purification and the confirmation of purity can be carried out by high performance liquid chromatography and polyacrylamide gel electrophoresis. The confirmation of molecular weight can be carried out by Electrospray Ionization Mass Spectrometry or Fast Atom Bombardment-Mass Spectrometry.

The expression-inhibiting substance against WT1 of the present invention is believed to inhibit the growth of solid tumor cells by acting in any stage from genomic DNA to mature mRNA and by inhibiting the expression thereof. Thus, the expression-inhibiting substance of the present invention is expected to be useful for the treatment of solid tumors.

The expression-inhibiting substance of the present invention can be mixed with an appropriate carrier material to formulate an external preparation such as a liniment, a cataplasm and the like.

It can also be mixed, as desired, with an excipient, an isotonic agent, a solubilizer, a stabilizer, an antiseptic, a soothing agent or the like to formulate a tablet, powder, granules, a capsule, a liposome capsule, an injection, a solution, a nasal drop, and the like as well as a lyophilized preparation. They can be prepared according to a conventional method.

The expression-inhibiting substance of the present invention may be applied to the patient by either directly administering it to the affected area of the patient or administering it into a blood vessel thereby allowing the substance to be delivered to the affected area. Furthermore, an encapsulating agent that enhances prolonged action and membrane permeability may be used. There may be mentioned, for example, liposome, poly-L-lysine, lipid, cholesterol, lipofectin or derivatives thereof.

Preferably the dosage of the expression-inhibiting substance of the present invention can be adjusted as appropriate depending on the condition, age, sex, weight, and the like of the patient to employ a preferred amount. The method of administration may be selected, as appropriate, from oral, intramuscular, intraperitoneal, intrathoracic, intraspinal, intratumoral, intradermal, subcutaneous, intravenous, intraarterial, rectal administration and the like to employ a preferred method.

The present invention is now explained in more detail with reference to the following examples.

EXAMPLES

Synthetic Example 1

The oligodeoxyribonucleotides (SEQ ID NO: 1 to 8) and the random sequence (Rand) used below were synthesized using an automatic synthetic instrument (Applied Biosystems), which were then purified by high performance liquid chromatography, were subjected to ethanol precipitation for three times, and then were suspended in a phosphate buffered saline.

The oligonucleotides that were synthesized are shown below. The random sequence (Rand) is a sequence comprising 18 nucleotides and thereby is theoretically a mixture of sequences of 4 to the 18th power kinds.

SEQ ID NO: 1: A sense sequence of the transcription capping site (SE1);

SEQ ID NO: 2: An antisense sequence of the transcription capping site (AS1);

SEQ ID NO: 3: A sense sequence of the transcription capping site;

SEQ ID NO: 4: An antisense sequence of the transcription capping site;

SEQ ID NO: 5: A sense sequence of the translation initiation region (SE2);

SEQ ID NO: 6: A antisense sequence of the translation initiation region (AS2);

SEQ ID NO: 7: A sense sequence of exon 6;

SEQ ID NO: 8: An antisense sequence of exon 6;

Example 1

Cells of the WT1 expression-positive gastric cancer AZ521 cell line at $5 \times 10^4$ cells/ml were inoculated at an amount of 100 µl/well into the RPMI1640 medium containing no fetal calf serum (FCS) in a flat-bottomed 96-well plate. The oligonucleotide AS1 or the control SE1 or rand was added to triple wells to a final concentration of 100 µg/ml. After incubation for 2 hours, FCS was added to each well to a final concentration of 10%. The oligonucleotide of half the above amount was added to the culture every 24 hours.

After incubation for 96 hours, the surviving cells were counted by the dye exclusion method. As a control culture, PBS having the same volume containing no nucleotides was added and the cell count in this culture was set as 100%.

Figure 1:
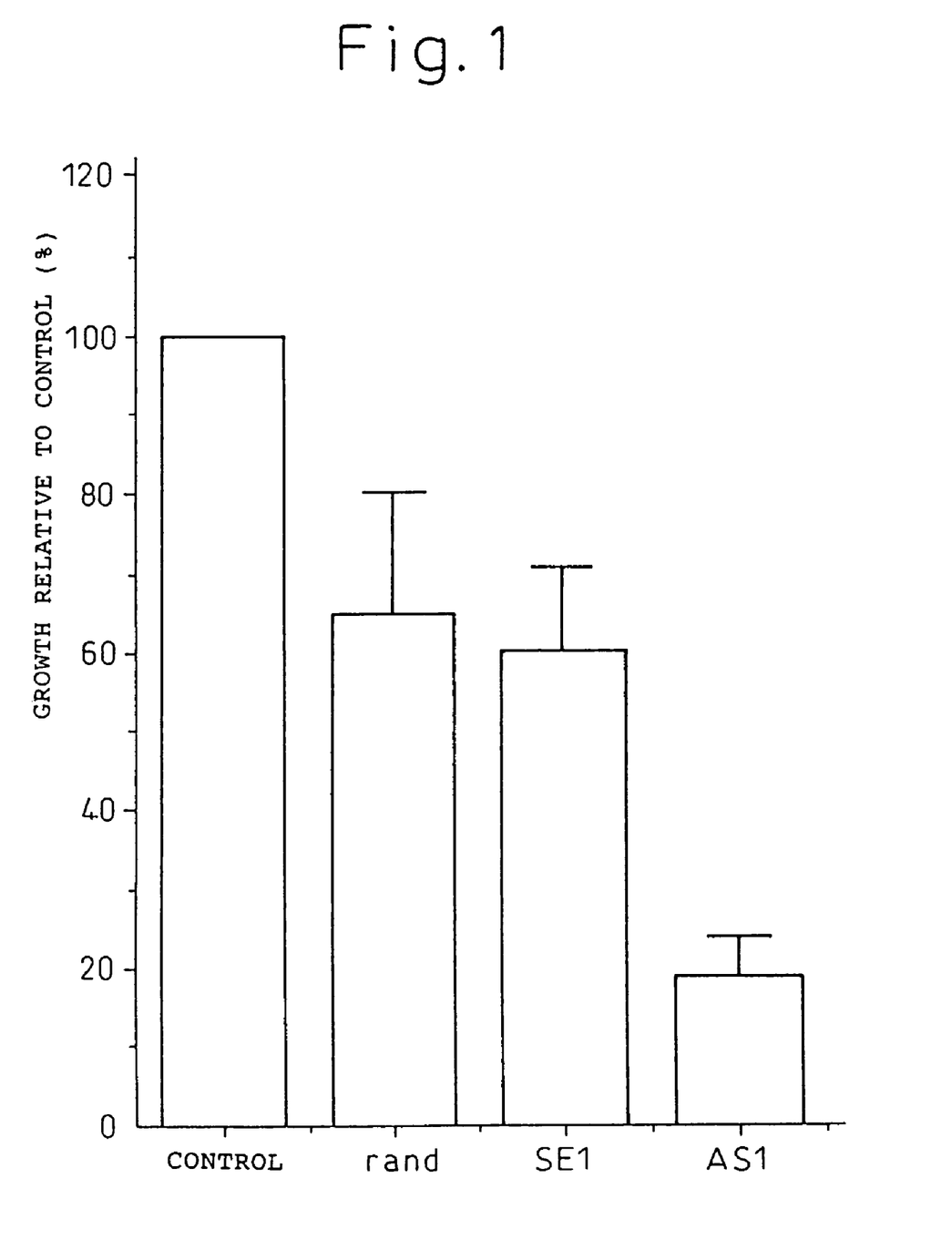
FIG. 1 is a graph showing an inhibitory effect of an oligonucleotide at 100 μg/ml on the cellular growth of the gastric cancer AZ521 cell line.

The result is shown in FIG. 1. As can be seen from this figure, the antisense oligonucleotide AS1 of the present invention strongly inhibited the growth of cells as compared to the corresponding sense oligonucleotide SE1.

Example 2

Figure 2:
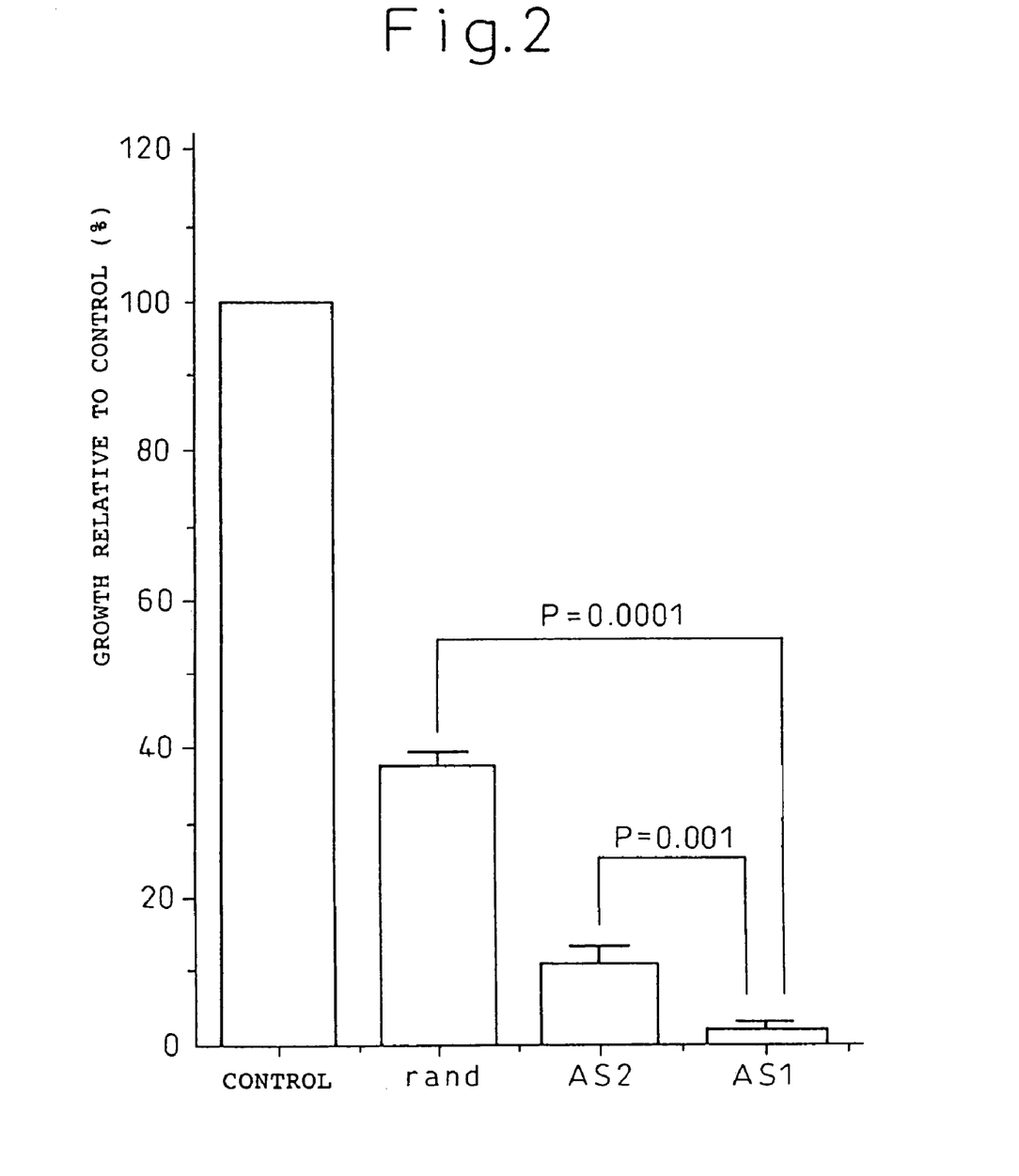
FIG. 2 is a graph showing an inhibitory effect of an oligonucleotide at 200 μg/ml on the cellular growth of the gastric cancer AZ521 cell line.

A similar experiment to the one described in Example 1 was carried out, except that the oligonucleotide AS1 or AS2, or rand was added at 200 μg/ml. As can be seen from FIG. 2, the antisense oligonucleotides AS1 and AS2 of the present invention significantly inhibited the growth of gastric cancer cells as compared to the random sequence (rand).

Example 3

Figure 3:
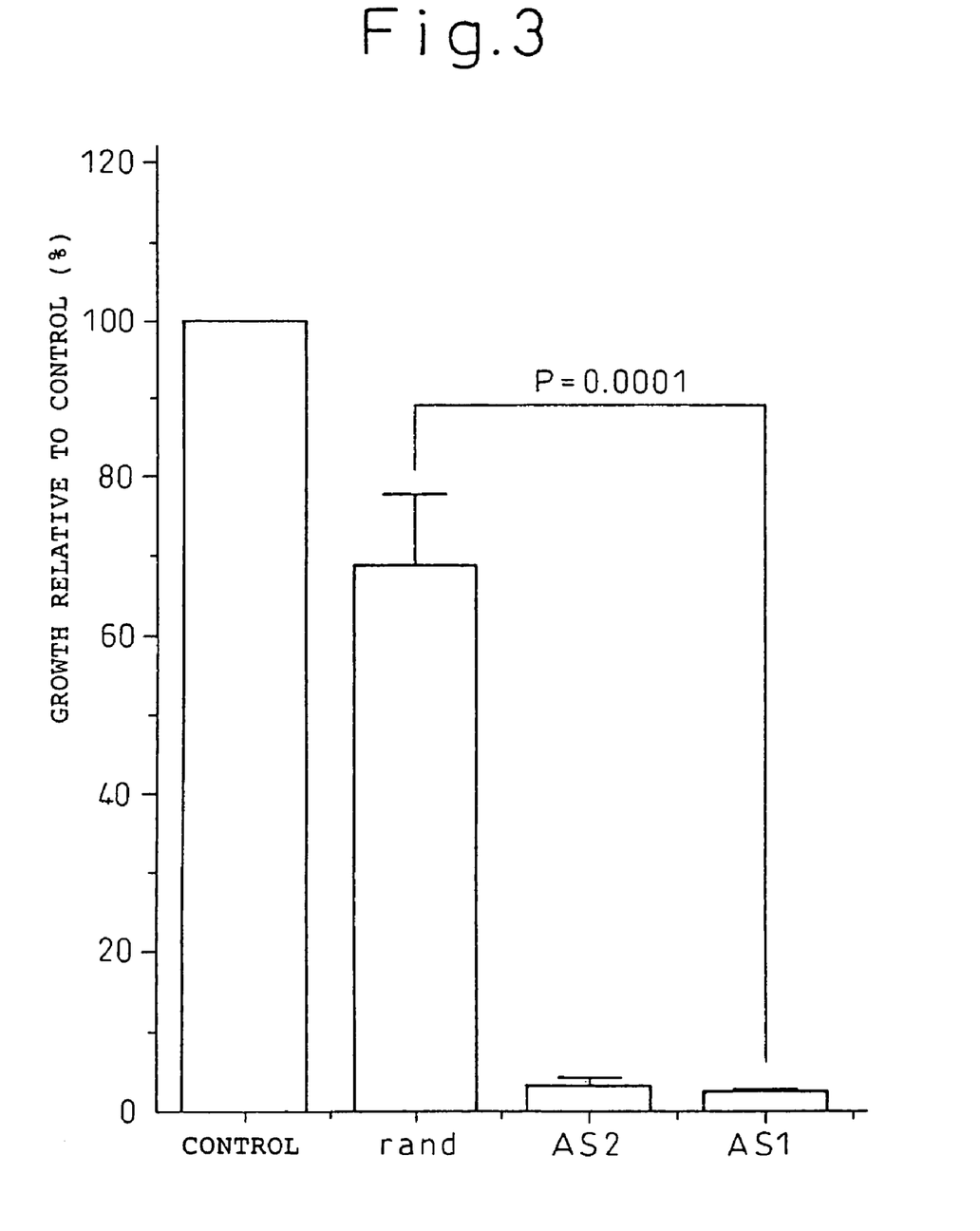
FIG. 3 is a graph showing an inhibitory effect of an oligonucleotide at 400 μg/ml on the cellular growth of the gastric cancer AZ521 cell line.

A similar experiment to the one described in Example 1 was carried out, except that the oligonucleotide AS1 or AS2, or rand was added at 400 μg/ml. As can be seen from FIG. 3, the antisense oligonucleotides AS1 and AS2 of the present invention significantly inhibited the growth of gastric cancer cells as compared to the random sequence (rand).

As is clear from the results in Examples 1 to 3, the inhibitory effect of the antisense oligonucleotide of the present invention on the growth of the gastric cancer cells was concentration-dependent.

Example 4

Figure 4:
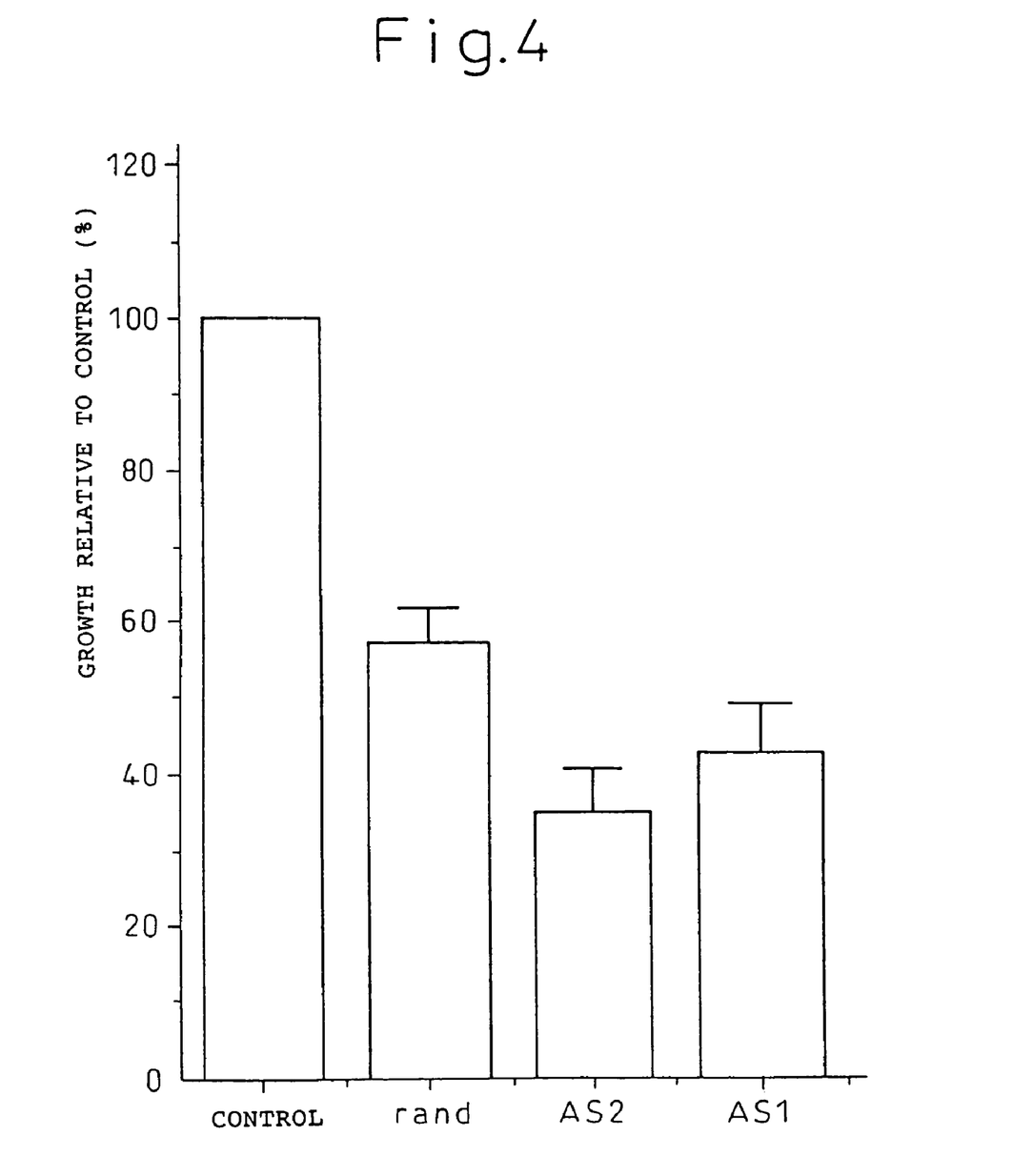
FIG. 4 is a graph showing an inhibitory effect of an oligonucleotide at 200 μg/ml on the cellular growth of the lung cancer OS3 cell line.

A similar experiment to the one described in Example 1 was carried out, except that cells of the lung cancer OS3 cell line were used as solid tumor cells, and the antisense oligonucleotide AS1 or AS2 or the random sequence (rand) was used at 200 μg/ml. As can be seen from FIG. 4, the antisense oligonucleotides AS1 and AS2 of the present invention significantly inhibited the growth of the lung cancer cells as compared to the random sequence (rand).

Example 5

Figure 5:
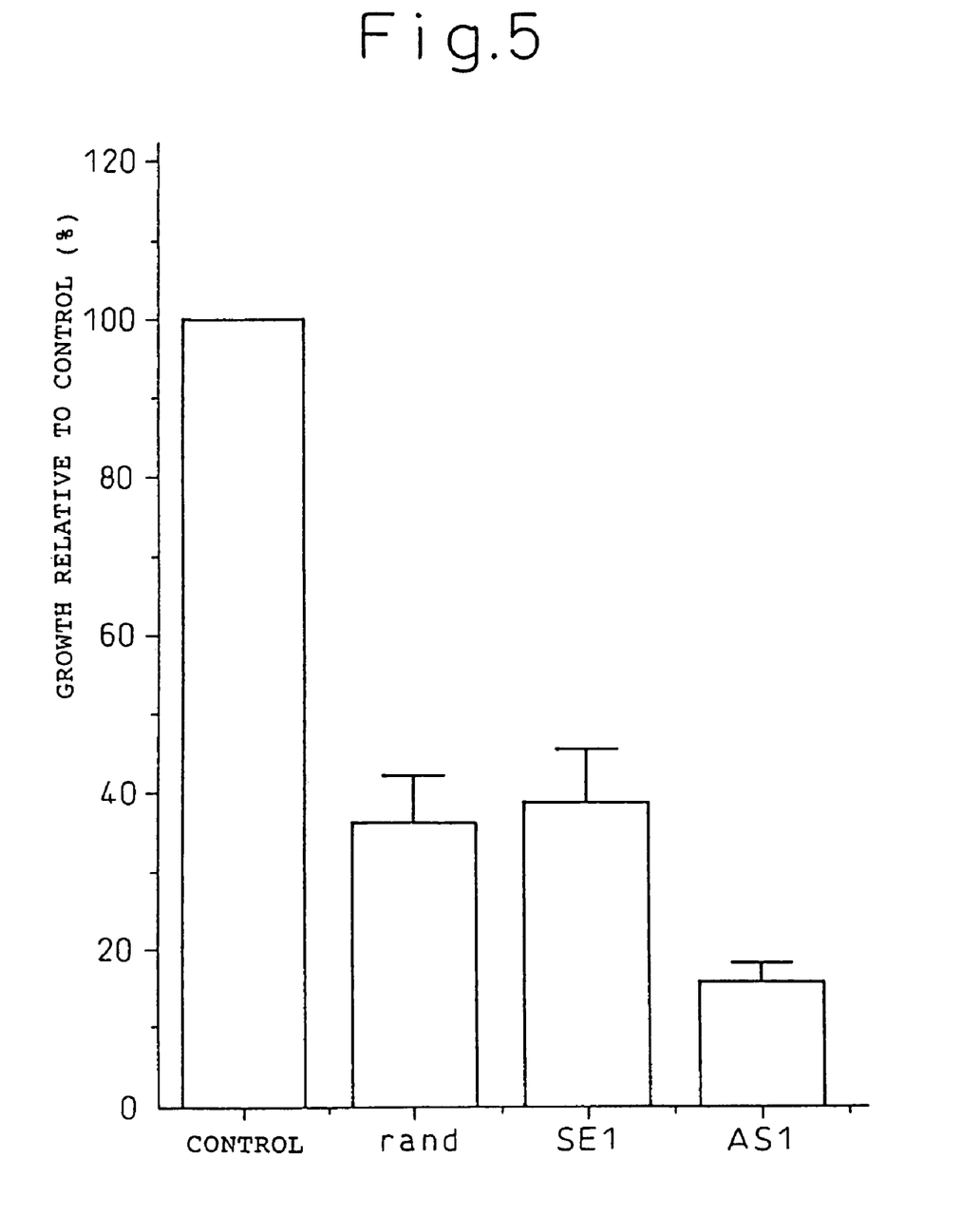
FIG. 5 is a graph showing an inhibitory effect of an oligonucleotide at 400 μg/ml on the cellular growth of the lung cancer OS3 cell line.

A similar experiment to the one described in Example 1 was carried out, except that the antisense oligonucleotide AS1 at 400 μg/ml or SE1 or rand at 400 μg/ml as a control were used. As can be seen from FIG. 5, the antisense oligonucleotide AS1 of the present invention significantly inhibited the growth of lung cancer cells as compared to the other control oligonucleotides.

As is clear from the comparisons in Examples 4 and 5, the inhibitory effect of the antisense oligonucleotide of the present invention on the growth of the lung cancer cells was concentration-dependent.

Example 6

Figure 6:
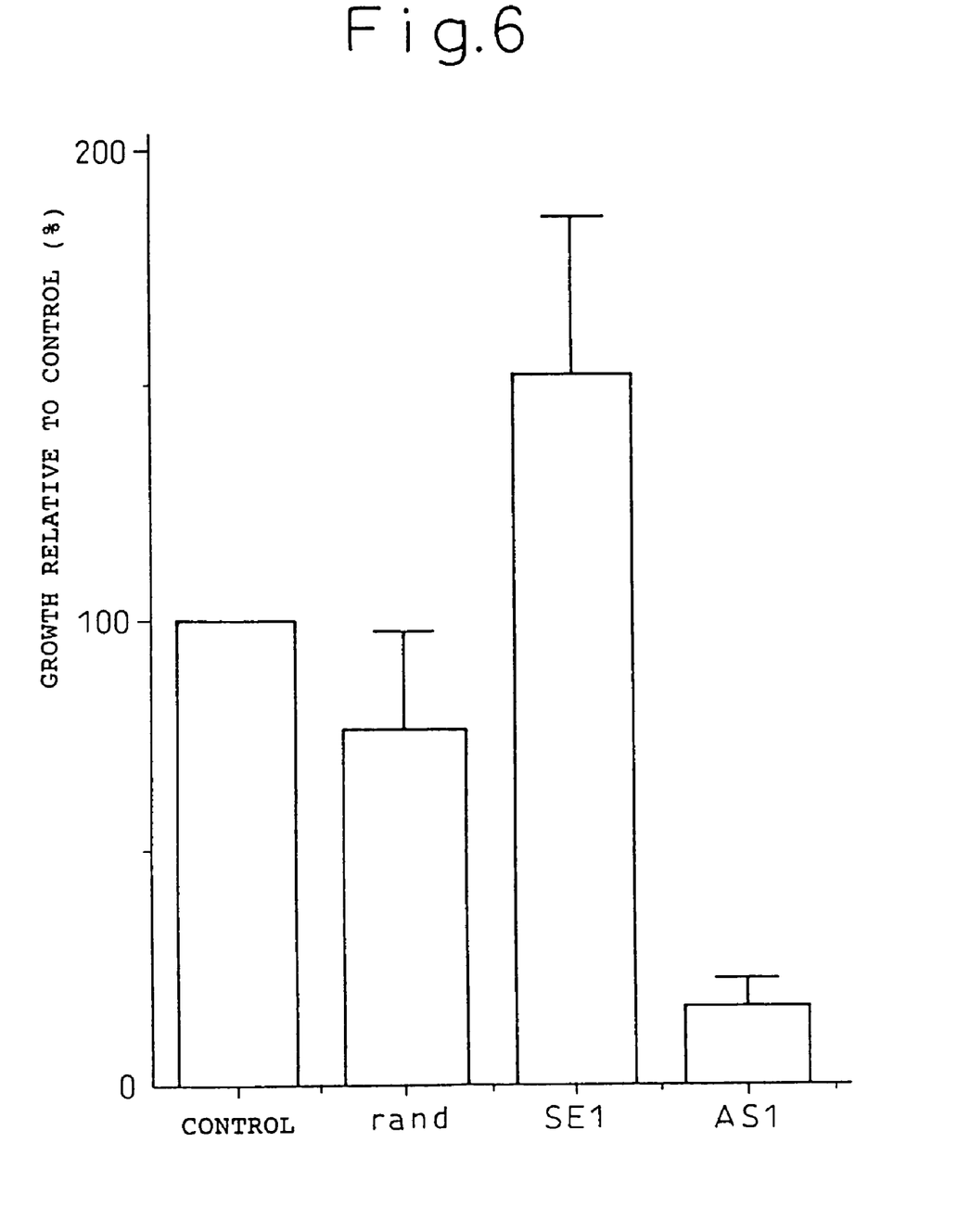
FIG. 6 is a graph showing an inhibitory effect of an oligonucleotide at 400 μg/ml on the cellular growth of the ovary cancer TYKnu cell line.

A similar experiment to the one described in Example 1 was carried out, except that the cells of the ovary cancer TYKnu cell line were used, the antisense oligonucleotide AS1 at 400 μg/ml or SE1 or the control oligonucleotide SE1 or rand at 400 μg/ml were used. As can be seen from FIG. 6, the antisense oligonucleotide AS1 of the present invention has shown a marked inhibitory effect on ovary cancer cells as compared to the control oligonucleotide.

Reference Example 1

Figure 7:
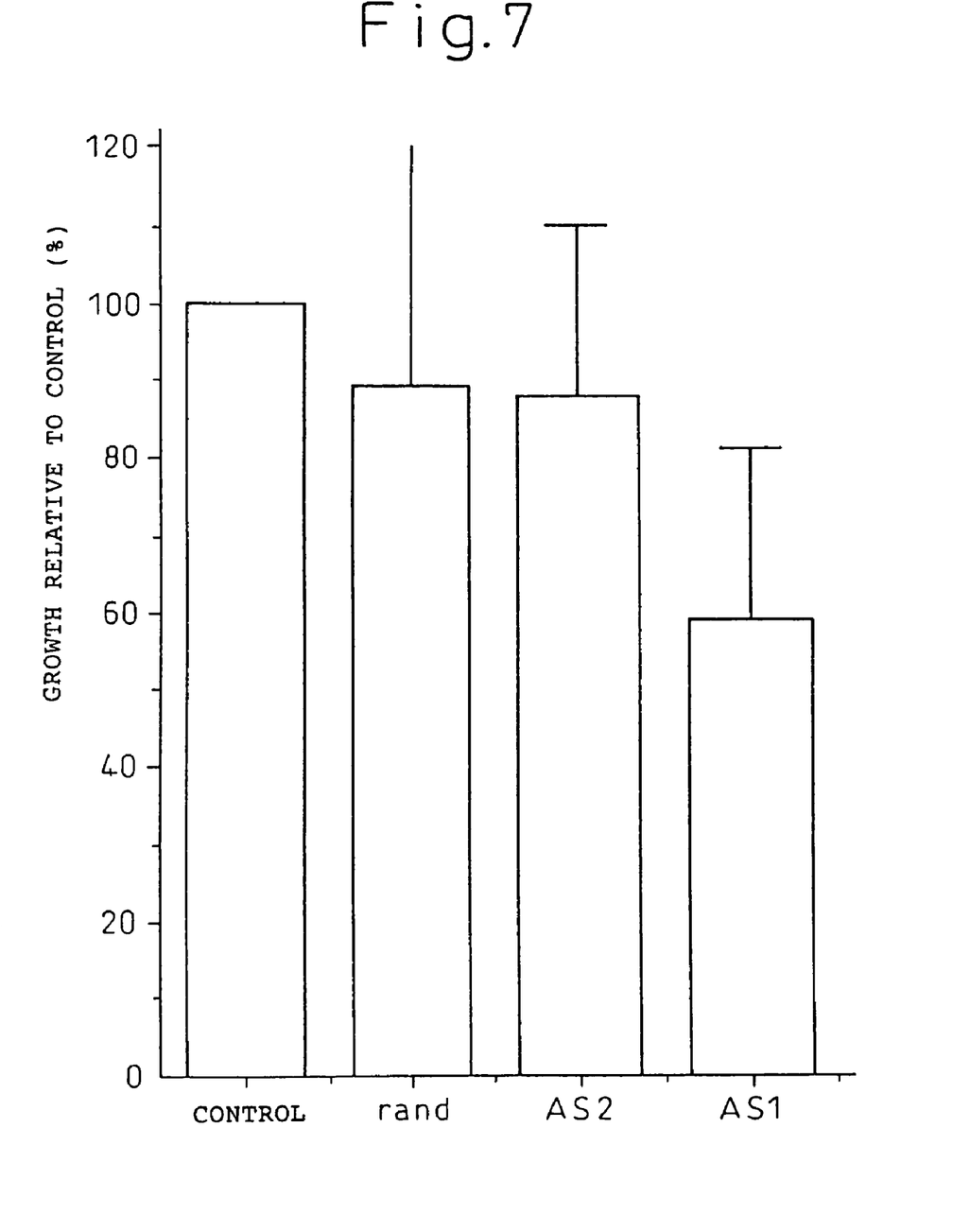
FIG. 7 is a graph showing an inhibitory effect of an oligonucleotide at 400 μg/ml on the cellular growth of WTAS PC14, a WT1-expression-negative lung adenocarcinoma cell line.

A similar experiment to those described in Examples was carried out, except that the cells of the WT1 expression-negative lung adenocarcinoma cell line WTAS PC14 were used as the test cells, the antisense oligonucleotide AS1 or AS2 at 400 μg/ml or the control oligonucleotide rand at 400 μg/ml were used. As can be seen from FIG. 7, the antisense oligonucleotide of the present invention did not exhibit a marked inhibitory effect on growth as compared to the WT1 expression-positive cells.

Example 7

RNA was extracted from each cancer cell line shown in Table 2 and the amount expressed of WT1 mRNA was determined using the RT-PCR method described below. The amount expressed of WT1 in the leukemia cell line K562 was set as 1.0 and the amount expressed of WT1 in each cancer cell line was shown at a relative amount in Table 2.

Total RNA from each cell line was extracted according to the conventional method [for example, the acid-guanidine-phenol-chloroform method: Anal. Biochem., 162, 156 (1987)]. The total RNA was dissolved in a diethyl pyrocarbonate-treated water, and then the absorbance at 260 nm was spectrophotometrically determined.

15.5 μl of the diethyl pyrocarbonate-treated water containing 1 μg of the total RNA was heated at 65° C. for 5 minutes, and was mixed with 14.5 μl of the RT buffer (50 mmol/l Tris HCl, pH 8.3; 70 mmol/l KCl; 3 mmol/l $MgCl_2$; 10 mmol/l dithiothreitol) containing 600 U of a reverse transcriptase (Moloney murine leukemia virus reverse transcriptase: GIBCO-BRL), 500 mmol/l of each deoxynucleotide triphosphate (dNTP: Pharmacia) and 750 ng of an olido dT primer and 40 U of an RNase inhibitor (Boehringer Mannheim).

The mixture was incubated at 37° C. for 90 minutes and heated at 70° C. for 20 minutes, and then was stored at −20° C. until use.

PCR was conducted using a DNA thermal cycler (Perkin Elmer-Cetus) at repeated cycles of denaturation at 94° C. for 1 minute, primer annealing at 64° C. for 1 minute (β actin: 60° C., 1 minute), and chain elongation at 72° C. for 2 minutes to obtain a PCR product (the first round PCR).

When the densitomer unit (described below) of said PCR product is less than 500, the second round PCR was carried out using nested inward primers in a reaction mixture comprising 2.5 μl of the first round PCR product.

The PCR product thus obtained was determined according to the method described in an article [J. Immunol., 147, 4307 (1991)] as described below:

Thus, the PCR product from 20 ng of total RNA was resolved on a 1.3% agarose gel containing 0.05 μg/ml ethidium bromide, and photographed with a Polaroid film (Polaroid 665 film, Polaroid Corp.).

The negative film was developed at 25° C. for 5 minutes and was assayed with a densitometer (CS-9000: Shimadzu) to obtain "densitomer units".

Furthermore, the result obtained from the above experiment using the PCR product in the absence of RNA was set as the negative control.

The primers used in the above experiment are as shown in Table 1.

TABLE 1

| First round PCR primer | Nucleotide sequence |
|---|---|
| Outward sense primer | 5'-GGCATCTGAGACCAGTGAGAA-3' (SEQ ID NO: 20) |
| Outward antisense primer | 5'-GAGAGTCAGACTTGAAAGCAGT-3' (SEQ ID NO: 21) |
| Second round PCR primer | Nucleotide sequence |
| Inward sense primer | 5'-GCTGTCCCACTTACAGATGCA-3' (SEQ ID NO: 22) |
| Inward antisense primer | 5'-TCAAAGCGCCAGCTGGAGTTT-3' (SEQ ID NO: 23) |

As primers for the β actin that was used as an internal control, those described in an article [Proc. Natl. Acad. Sci. U.S.A. 82, 6133 (1985)] were used. Each of these primers was chemically synthesized according to a conventional method.

In order to standardize the differences in the amount used of RNA in RT-PCR and RNA degradation in each sample, the result of the WT1 gene (densitometer units) was divided by that of β actin, which was set as the level of the WT1 gene expression.

The result is shown in Table 2.

TABLE 2

| Origin | Cell line | Amount expressed of WT |
|---|---|---|
| Gastric cancer | AZ 521 | $1.2 \times 10^{0}$ |
| Colon cancer | LOVO | $1.1 \times 10^{-3}$ |
|  | SW 480 | $2.3 \times 10^{-1}$ |
|  | SW 620 | $1.0 \times 10^{-1}$ |
|  | COLO 320 DM | $7.3 \times 10^{-3}$ |
| Lung cancer | OS 1 | $1.6 \times 10^{-2}$ |
|  | OS 2R | $8.3 \times 10^{-3}$ |

TABLE 2-continued

| Origin | Cell line | Amount expressed of WT |
|---|---|---|
|  | OS 3 | $3.1 \times 10^{-2}$ |
|  | LU 99B | $2.9 \times 10^{-2}$ |
|  | LU 99C | $3.4 \times 10^{-2}$ |
|  | VMRC-LCP | $4.9 \times 10^{-1}$ |
| Breast cancer | MDA MB 231 | $3.3 \times 10^{-2}$ |
|  | YMB 1 | $5.2 \times 10^{-2}$ |
| Embryonic cell cancer | NEC 8 | $5.8 \times 10^{-3}$ |
| Ovary cancer | TYK NU | $4.5 \times 10^{-1}$ |
|  | TYK nu. CP-r | $2.5 \times 10^{-1}$ |
| Leukemia (control) | K 562 | $1.0 \times 10^{-0}$ |

The above result confirmed that the WT1 gene is expressed in the cultured cell lines derived from various solid tumors.

As hereinabove stated, the antisense oligonucleotides of the present invention are useful for inhibiting the growth of solid tumor cells and thereby are expected to be novel therapeutic agents for treatment of solid tumors.

The invention claimed is:

1. A method for inhibiting growth of solid tumor cells by contacting said tumor cells with an antisense oligonucleotide selected from the group consisting of:
   (a) SEQ ID NO: 2; and
   (b) a modified antisense oligonucleotide of SEQ ID NO: 2, wherein the modification is selected from the group consisting of modification with lower alkyl phosphonate, phosphorothioate, phosphorodithioate, phosphoroamidate and triester phosphate, and wherein the solid tumor is gastric cancer, colon cancer, lung cancer, breast cancer, embryonic cell cancer, or ovary cancer.

2. A method for treatment of a patient suffering from a solid tumor, comprising administering to said patient an antisense oligonucleotide selected from the group consisting of:
   (a) SEQ ID NO: 2; and
   (b) and a modified antisense oligonucleotide of SEQ ID NO: 2, wherein the modification is selected from the group consisting of lower alkyl phosphonate, phosphorothioate, phosphorodithioate, phosphoroamidate and triester phosphate, and wherein the solid tumor is gastric cancer, colon cancer, lung cancer, breast cancer, embryonic cell cancer, or ovary cancer.

3. The method according to claim 1, wherein the solid tumor is gastric cancer, colon cancer, lung cancer or breast cancer.

4. The method according to claim 2, wherein the solid tumor is gastric cancer, colon cancer, lung cancer or breast cancer.

5. The method according to claim 1, wherein the oligonucleotide is administered to the affected area of the patient.

6. The method according to claim 2, wherein the oligonucleotide is administered to the affected area of the patient.

* * * * *

SEQUENCE LISTING

```
<160> NUMBER OF SEQ ID NOS: 23

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
cccaccgcat tcgaccct                                                    18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA
```

```
<400> SEQUENCE: 2
agggtcgaat gcggtggg                                                18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ccggcccctc ttatttga                                                18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tcaaataaga ggggccgg                                                18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
cagcaaatgg gctccgac                                                18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gtcggagccc atttgctg                                                18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
agcgataacc acacaacg                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA
```

<400> SEQUENCE: 8
cgttgtgtgg ttatcgct                                                        18

<210> SEQ ID NO 9
<211> LENGTH: 1272
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
tggtatcctc gaccagggcc acaggcagtg ctcggcggag tggctccagg agttacccgc        60
tccctgccgg gcttcgtatc caaaccctcc ccttcacccc tcctcccaa actgggcgcc        120 aggatgctcc ggccggaata tacgcaggct ttgggcgttt gccaagggtt ttcttccctc       180
ctaaactagc cgctgttttc ccggcttaac cgtagaagaa ttagatattc ctcactggaa       240
agggaaacta agtgctgctg actccaattt taggtaggcg gcaaccgcct ccgcctggc        300 gcaaacctca ccaagtaaac aactactagc cgatcgaaat acgcccggct tataactggt       360
gcaactcccg gccacccaac tgagggacgt tcgctttcag tcccgacctc tggaaccac        420 aaagggccac ctcttttccc agtgacccca agatcatggc cactcccta cccgacagtt       480 ctagagcaag agccagactc aagggtgcaa agcaagggta tacgcttctt tgaagcttga      540
ctgagttctt tctgcgcttt cctgaagttc ccgccctctt ggagcctacc tgcccctccc      600
tccaaaccac tcttttagat taacaacccc atctctactc ccaccgcatt cgaccctgcc      660
cggactcact gctactgaac ggactctcca gtgagacgag gctcccacac tggcgaaggc      720 aagaaggga ggtggggga gggttgtgcc acaccggcca gctgagagcg cgtgttgggt        780
tgaagaggag ggtgtctccg agagggacgc tccctcggac ccgccctcac cccagctgcg      840
agggcgcccc caaggagcag cgcgcgctgc ctggccgggc ttgggctgct gagtgaatgg      900
agcggccgag cctcctggct cctcctcttc cccgcgccgc cggcccctct tatttgagct      960
ttgggaagct gagggcagcc aggcagctgg ggtaaggagt tcaaggcagc gcccacaccc     1020
gggggctctc cgcaacccga ccgcctgtcg ctccccccact tcccgccctc cctcccacct    1080
actcattcac ccacccaccc acccagagcc gggacggcag cccaggcgcc cgggccccgc     1140
cgtctcctcg ccgcgatcct ggacttcctc ttgctgcagg acccggcttc cacgtgtgtc     1200
ccggagccgg cgtctcagca cacgctccgc tccgggcctg ggtgcctaca gcagccagag    1260
cagcagggag tc                                                           1272

<210> SEQ ID NO 10
<211> LENGTH: 457
<212> TYPE: DNA
<213> ORGANISM: Artificial Sequence
<220> FEATURE:
<223> OTHER INFORMATION: Description of Artificial Sequence: Synthetic
      DNA - a part of exon 1 of WT1 gene

<400> SEQUENCE: 10
tctgagcctc agcaaatggg ctccgacgtg cgggacctga acgcgctgct gcccgccgtc        60
ccctccctgg gtggcggcgg cggctgtgcc ctgcctgtga cggcgcggc gcagtgggcg       120 ccggtgctgg actttgcgcc cccgggcgct tcggcttacg ggtcgttggg cggccccgcg       180
ccgccaccgg ctccgccgcc acccccgccg ccgccgcctc actccttcat caaacaggag       240
ccgagctggg gcggcgcgga gccgcacgag gagcagtgcc tgagcgcctt cactgtccac      300

```
ttttccggcc agttcactgg cacagccgga gcctgtcgct acgggccctt cggtcctcct    360
ccgcccagcc aggcgtcatc cggccaggcc aggatgtttc taacgcgcc ctacctgccc     420 agctgcctcg agagccagcc cgctattcgc aatcagg                             457

<210> SEQ ID NO 11
<211> LENGTH: 123
<212> TYPE: DNA
<213> ORGANISM: Artificial Sequence
<220> FEATURE:
<223> OTHER INFORMATION: Description of Artificial Sequence: Synthetic
      DNA - exon 2 of WT1 gene

<400> SEQUENCE: 11
gttacagcac ggtcaccttc gacgggacgc ccagctacgg tcacacgccc tcgcaccatg     60
cggcgcagtt ccccaaccac tcattcaagc atgaggatcc catgggccag cagggctcgc    120
tgg                                                                  123

<210> SEQ ID NO 12
<211> LENGTH: 103
<212> TYPE: DNA
<213> ORGANISM: Artificial Sequence
<220> FEATURE:
<223> OTHER INFORMATION: Description of Artificial Sequence: Synthetic
      DNA - exon 3 of WT1 gene

<400> SEQUENCE: 12
gtgagcagca gtactcggtg ccgccccgg tctatggctg ccacacccc accgacagct      60 gcaccggcag ccaggctttg ctgctgagga cgccctacag cag                      103

<210> SEQ ID NO 13
<211> LENGTH: 78
<212> TYPE: DNA
<213> ORGANISM: Artificial Sequence
<220> FEATURE:
<223> OTHER INFORMATION: Description of Artificial Sequence: Synthetic
      DNA - exon 4 of WT1 gene

<400> SEQUENCE: 13
tgacaattta taccaaatga catcccagct tgaatgcatg acctggaatc agatgaactt     60
aggagccacc ttaaaggg                                                  78

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      DNA - exon 5 of WT1 gene

<400> SEQUENCE: 14
agttgctgct gggagctcca gctcagtgaa atggacagaa gggcagagca a              51

<210> SEQ ID NO 15
<211> LENGTH: 97
<212> TYPE: DNA
<213> ORGANISM: Artificial Sequence
<220> FEATURE:
<223> OTHER INFORMATION: Description of Artificial Sequence: Synthetic
      DNA - exon 6 of WT1 gene

<400> SEQUENCE: 15
ccacagcaca gggtacgaga gcgataacca cacaacgccc atcctctgcg agcccaata     60
```
cagaatacac acgcacggtg tcttcagagg cattcag                                    97

<210> SEQ ID NO 16
<211> LENGTH: 151
<212> TYPE: DNA
<213> ORGANISM: Artificial Sequence
<220> FEATURE:
<223> OTHER INFORMATION: Description of Artificial Sequence: Synthetic
      DNA - exon 7 of WT1 gene

<400> SEQUENCE: 16
gatgtgcgac gtgtgcctgg agtagccccg actcttgtac ggtcggcatc tgagaccagt     60
gagaaacgcc ccttcatgtg tgcttaccca ggctgcaata agagatattt taagctgtcc    120
cacttacaga tgcacagcag gaagcacact g                                   151

<210> SEQ ID NO 17
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA - exon 8 of WT1 gene

<400> SEQUENCE: 17
gtgagaaacc ataccagtgt gacttcaagg actgtgaacg aaggttttct cgttcagacc     60
agctcaaaag acaccaaagg agacatacag                                     90

<210> SEQ ID NO 18
<211> LENGTH: 93
<212> TYPE: DNA
<213> ORGANISM: Artificial Sequence
<220> FEATURE:
<223> OTHER INFORMATION: Description of Artificial Sequence: Synthetic
      DNA - exon 9 of WT1 gene

<400> SEQUENCE: 18
gtgtgaaacc attccagtgt aaaacttgtc agcgaaagtt ctcccggtcc gaccacctga     60
agacccacac caggactcat acaggtaaaa caa                                 93

<210> SEQ ID NO 19
<211> LENGTH: 158
<212> TYPE: DNA
<213> ORGANISM: Artificial Sequence
<220> FEATURE:
<223> OTHER INFORMATION: Description of Artificial Sequence: Synthetic
      DNA - a part of exon 10 of WT1 gene

<400> SEQUENCE: 19
gtgaaaagcc cttcagctgt cggtggccaa gttgtcagaa aaagtttgcc cggtcagatg     60
aattagtccg ccatcacaac atgcatcaga gaaacatgac caaactccag ctggcgcttt    120
gaggcgtctc cctcggggac cgttcagtgt cccaggca                            158

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
ggcatctgag accagtgaga a                                              21

```
<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gagagtcaga cttgaaagca gt                                              22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
gctgtcccac ttacagatgc a                                               21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
tcaaagcgcc agctggagtt t                                               21
```